US008362312B2

(12) United States Patent
Brookhart et al.

(10) Patent No.: US 8,362,312 B2
(45) Date of Patent: *Jan. 29, 2013

(54) SUPPORTED IRIDIUM CATALYSTS (75) Inventors: Maurice Brookhart, Carrboro, NC (US); Alan Goldman, Highland Park, NJ (US); Emily Carson, Raleigh, NC (US); Zheng Huang, Irbana, IL (US); Sabuj Kumar Kundu, Rochester, NY (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 86 days.

This patent is subject to a terminal disclaimer.

(21) Appl. No.: 12/663,044

(22) PCT Filed: Jun. 4, 2008

(86) PCT No.: PCT/US2008/007006
§ 371 (c)(1),
(2), (4) Date: May 26, 2010

(87) PCT Pub. No.: WO2008/153869
PCT Pub. Date: Dec. 18, 2008

(65) Prior Publication Data
US 2010/0236984 A1 Sep. 23, 2010

Related U.S. Application Data (60) Provisional application No. 60/942,070, filed on Jun. 5, 2007.

(51) Int. Cl.
*C10G 11/02* (2006.01)

(52) U.S. Cl. ........ 585/656; 208/121; 208/113; 502/100; 502/321; 502/305; 502/325; 585/708

(58) Field of Classification Search .................. 208/113, 208/121; 502/100, 305, 321, 325; 585/310, 585/324, 444, 644, 646, 647, 656, 709
See application file for complete search history.

(56) References Cited

U.S. PATENT DOCUMENTS

| 6,566,568 | B1 | 5/2003 | Chen et al. | |
| 6,566,569 | B1 | 5/2003 | Chen et al. | |
| 6,982,305 | B2 | 1/2006 | Nagy | |
| 2004/0181104 | A1* | 9/2004 | Yeh et al. | 585/444 |
| 2007/0060781 | A1 | 3/2007 | Goldman et al. | |

OTHER PUBLICATIONS

International Search Report and Written Opinion, PCT/US2008/007006, mailed Dec. 23, 2008.

* cited by examiner

*Primary Examiner* — In Suk Bullock
*Assistant Examiner* — Sharon Pregler
(74) *Attorney, Agent, or Firm* — Myers Bigel Sibley & Sajovec, P.A.

(57) ABSTRACT

A method of converting at least one first alkane to a mixture of at least one low molecular weight alkane (optionally also including additional lower and/or higher molecular weight alkanes) and at least one high molecular weight alkane, comprises: reacting a first alkane in the presence of dual catalyst system comprising a first catalyst (i.e., a hydrogen transfer catalyst) and a second catalyst (i.e., a metathesis catalyst) to produce a mixture of low and high molecular weight alkanes.

26 Claims, 2 Drawing Sheets

SUPPORTED IRIDIUM CATALYSTS

RELATED APPLICATIONS

This application is a 35 U.S.C. §371 national phase application of PCT Application PCT/US2008/007006, filed Jun. 4, 2008, and published in English on Dec. 18, 2008, as International Publication No. WO 2008/153869, and which claims the benefit of U.S. Provisional Patent Application Ser. No. 60/942,070, filed Jun. 5, 2007, and is also related to Goldman et al., U.S Patent Application Publication No. 2007/0060781, the disclosure of each of which is incorporated by reference herein in its entirety.

GOVERNMENT FUNDING

This invention was made with Government support under Grant No. CHE-0107810 from the National Science Foundation. The United States Government has certain rights to this invention.

FIELD OF THE INVENTION

The present invention concerns methods of converting alkanes to higher molecular weight alkanes and fuels such as diesel fuel, along with catalyst systems and apparatus useful in such methods.

BACKGROUND OF THE INVENTION

Rising demand for fuels and potentially diminishing supplies of crude oil (or at least limits in or volatility in the capacity to manufacture fuels from crude oil) have spurred increased interest in the production of fuels from alternative sources.

Coal, natural gas and biomass can be converted to synthesis gas (generally composed of hydrogen and carbon monoxide) in accordance with known techniques. Synthesis gas can, in turn, be converted to liquid hydrocarbons by the well-known technique of Fischer-Tropsch catalysis, which has been utilized for the production of fuels for many years. See, e.g., M. Dry, High quality diesel via the Fischer-Tropsch process—A review, *J. Chem. Technol. Biotechnol.* 77: 43-50 (2001). Fischer-Tropsch catalysis, however, produces a mixture of alkanes, many of which are of lower molecular weight and unsuitable for use as liquid hydrocarbon fuels such as gasoline and diesel fuels.

Some examples of dual catalyst systems are described in R. Burnett and T. Hughes, Mechanism and Poisoning of the Molecular Redistribution Reaction of Alkanes with a Dual-Functional Catalyst System, *J. Catalysis* 31, 55-64 (1973) (See also U.S. Pat. No. 6,566,568 to Chen). These techniques have not been widely implemented. Accordingly, there is a need for new ways to convert lower molecular weight alkanes to higher molecular weight alkanes useful as liquid hydrocarbon fuels.

SUMMARY OF THE INVENTION

A first aspect of the present invention is a method of converting at least one first alkane to a mixture of at least one low molecular weight alkane (optionally also including additional lower and/or higher molecular weight alkanes) and at least one high molecular weight alkane, comprising: reacting a first alkane in the presence of dual catalyst system comprising a first catalyst (i.e., a hydrogen transfer catalyst) and a second catalyst (i.e., a metathesis catalyst) to produce a mixture of low and high molecular weight alkanes.

In some embodiments of the foregoing, the invention provides a method of converting at least one low molecular weight alkane and at least one high molecular weight alkane to at least one medium molecular weight alkane, comprising: reacting at least one low molecular weight alkane and at least one high molecular weight alkane in the presence of a dual catalyst system comprising a first catalyst (i.e., a hydrogen transfer catalyst) and a second catalyst (i.e., a metathesis catalyst) to produce said at least one medium molecular weight alkanes.

The first alkane or starting alkane or alkanes can, in some embodiments, be produced by Fischer Tropsch catalysis of a synthesis gas. Fuels such as diesel fuel and gasoline can be produced from the either the high or low molecular weight alkane products (depending upon the molecular weight of the first alkane (e.g., liquid vs. wax product of a Fischer Tropsch reaction).

The reaction step can be carried out in any suitable form, including as a batch reaction or continuous reaction, and as a heterogeneous reaction (that is, with immobilized catalyst), as a homogeneous reaction (that is, with solubilized catalyst), or as a mixed system (that is, with one catalyst immobilized and the other catalyst solubilized).

A second aspect of the invention is a composition comprising, in combination, (i) a hydrogen transfer catalyst immobilized on a solid support; and (ii) a metathesis catalyst immobilized on a solid support (which may be the same as, or different from the solid support on which the hydrogen transfer catalyst is immobilized).

The foregoing and other objects and aspects of the present invention are explained in greater detail in the drawings herein and the specification set forth below.

BRIEF DESCRIPTION OF THE DRAWINGS

FIG. 1 is a schematic illustration of an apparatus of the present invention. Dual catalysts in reactor 20 may be combined in a single reactor vessel or physically separated from one another, as illustrated further in FIGS. 2-3.

DETAILED DESCRIPTION OF THE PREFERRED EMBODIMENTS

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

The disclosures of all United States patents cited herein are to be incorporated herein by reference in their entirety.

1. First alkane supply. The first alkane used to carry out the present invention can be a single alkane or a mixture of alkanes containing the identified alkane, or range of alkanes, to be reacted. The first alkane can be provided in a hydrocarbon feed composition from any suitable source, in accordance with known techniques such as fractional distillation, cracking, reforming, dehydrogenation, etc (including combinations thereof). One suitable source described further herein, by no means to be taken as limiting of the present invention, is the output of a Fischer-Tropsch reaction system.

The present invention is useful for, among other things, converting the lower molecular weight alkanes produced by a Fischer Tropsch reaction to higher molecular weight alkanes more useful as fuels for internal combustion engines, such as gasoline and diesel fuel.

The production of hydrocarbon compositions comprising alkanes from synthesis gas by Fischer-Tropsch catalysis is well known and may be carried out in accordance with known techniques by reaction of a synthesis gas in the presence of Fischer-Tropsch catalyst in a reactor. Any suitable catalyst can be used, including but not limited to iron and cobalt catalysts. See, e.g., U.S. Pat. No. 6,217,830 to Roberts and Kilpatrick; see also U.S. Pat. Nos. 6,880,635; 6,838,487; 6,201,030; 6,068,760; 5,821,270; 5,817,701; 5,811,363; 5,620,676; and 2,620,347.

The production of synthesis gas from carbonaceous or organic materials such as coal (including coal fines), natural gas, methane, refinery bottoms, vegetative materials such as wood or other biomass, and combinations thereof, is well known and can be carried out in accordance with known techniques. In some embodiments such production involves the partial oxidation of the carbonaceous or organic material at elevated temperatures, and optionally elevated pressures, with a limited volume of oxygen. The reaction is preferably carried out in a reactor into which the material is fed, together with additional agents such as steam, carbon dioxide, or various other materials. See e.g., U.S. Pat. No. 4,959,080; see also U.S. Pat. No. 4,805,561.

2. Hydrogen transfer catalysts. Hydrogen transfer catalysts useful for carrying out the present invention are known and described in, for example, U.S. Pat. Nos. 5,744,667; 5,585,530; 5,461,182; 5,227,552 and 3,321,545. Other examples of platinum, rhodium and ruthenium catalysts supported on zeolites and alumina are set forth in R. G. Pellet, *Journal of Catalysis* 177, 40-52 (1998); and S. Naito and M. Tanimoto, *J. Mol. Catal. A: Chemical* 141, 205-214 (1999).

Other examples are iridium catalysts, including but not limited to those described in U.S. Pat. No. 5,780,701; and in:

Goettker-Schnetmann, I., White, P., Brookhart, M., "Iridium Bis(Phosphinite)p-xPCP Pincer Complexes Highly Active Catalysts for the Transfer Dehydrogenation of Alkanes" J. Am. Chem. Soc. 2004, 126, 1804-1811; Crabtree, R. H.; Mellea, M. F.; Mihelcic, J. M.; Quirk, J. M. "Alkane dehydrogenation by iridium complexes" *J. Am. Chem. Soc.* 1982, 104, 107-13; Felkin, H.; Fillebeen-Khan, T.; Holmes-Smith, R.; Lin, Y. "Activation of carbon-hydrogen bonds in saturated hydrocarbons. The selective, catalytic functionalization of methyl groups by means of a soluble iridium polyhydride system" *Tetrahedron Lett.* 1985, 26, 1999-2000; Burk, M. J.; Crabtree, R. H. "Selective catalytic dehydrogenation of alkanes to alkenes" *J. Am. Chem. Soc.* 1987, 109, 8025-32; Maguire, J. A.; Goldman, A. S. "Efficient Low-Temperature Thermal Functionalization of Alkanes. Transfer-Dehydrogenation Catalyzed by Rh(PMe$_3$)$_2$(CO)Cl in Solution Under High Pressure Dihydrogen Atmosphere" *J. Am. Chem. Soc.* 1991, 113, 6706-6708; Maguire, J. A.; Petrillo, A.; Goldman, A. S. "Efficient Transfer-Dehydrogenation of Alkanes Catalyzed by Rhodium Trimethylphosphine Complexes Under Dihydrogen Atmosphere" *J. Am. Chem. Soc.* 1992, 114, 9492-9498; Gupta, M.; Hagen, C.; Flesher, R. J.; Kaska, W. C.; Jensen, C. M. "A highly active alkane dehydrogenation catalyst: stabilization of dihydrido Rh and Ir complexes by a P—C—P pincer ligand" *Chem. Commun.* 1996, 2083-2084; Wang, K.; Goldman, M. E.; Emge, T. J.; Goldman, A. S. "Transfer-Dehydrogenation of Alkanes Catalyzed by Rhodium(I) Phosphine Complexes" *J. Organomet. Chem.* 1996, 518, 55-68; Gupta, M.; Hagen, C.; Kaska, W. C.; Cramer, R. E.; Jensen, C. M. "Catalytic Dehydrogenation of Cycloalkanes to Arenes by a Dihydrido Iridium P—C—P Pincer Complex" *J. Am. Chem. Soc.* 1997, 119, 840-841; Gupta, M.; Kaska, W. C.; Jensen, C. M. "Catalytic Dehydrogenation of Ethylbenzene and THF by a Dihydrido Iridium P—C—P Pincer Complex" *Chem. Commun.* 1997, 461-462; Xu, W.; Rosini, G. P.; Gupta, M.; Jensen, C. M.; Kaska, W. C.; Krogh-Jespersen, K.; Goldman, A. S. "Thermochemical Alkane Dehydrogenation Catalyzed in Solution Without the Use of a Hydrogen Acceptor" *Chem. Commun.* 1997, 2273-2274; Liu, F.; Pak, E. B.; Singh, B.; Jensen, C. M.; Goldman, A. S. "Dehydrogenation of n-Alkanes Catalyzed by Iridium "Pincer" Complexes. Regioselective Formation of Alpha-Olefins" *J. Am. Chem. Soc.* 1999, 121, 4086-4087; Liu, F.; Goldman, A. S. "Efficient thermochemical alkane dehydrogenation and isomerization catalyzed by an iridium pincer complex" *Chem. Commun.* 1999, 655-656; Jensen, C. M. "Iridium PCP pincer complexes: highly active and robust catalysts for novel homogeneous aliphatic dehydrogenations" *Chem. Commun.* 1999, 2443-2449; Krogh-Jespersen, K.; Czerw, M.; Summa, N.; Renkema, K. B.; Achord, P. D.; Goldman, A. S. "On the Mechanism of (PCP)Ir-catalyzed Acceptorless Dehydrogenation of Alkanes: a Combined Computational and Experimental Study" *J. Am. Chem. Soc.* 2002, 124, 11404-11416; and Zhu, K.; Achord, P. D.; Zhang, X.; Krogh-Jespersen, K.; Goldman, A. S. "Highly Effective Pincer-Ligated Iridium Catalysts for Alkane Dehydrogenation. DFT Calculations of Relevant Thermodynamic, Kinetic, and Spectroscopic Properties" *J. Am. Chem. Soc.* 2004, 126, 13044-13053.

In a preferred embodiment, the hydrogen transfer catalyst is an iridium pincer complex catalyst, such as described above, and also described in U.S. Pat. No. 6,982,305 to Nagy. Examples of such catalysts include but are not limited to compounds of Formula (I):

(I)

wherein:
each R is independently H or a $C_1$-$C_{30}$ hydrocarbyl radical;
each $R_1$ is independently a $C_1$-$C_{30}$ hydrocarbyl radical; and
each X is independently selected from O and $CH_2$.

3. Olefin metathesis catalysts. Numerous olefin metathesis catalysts, including heterogeneous catalysts and homogeneous catalysts, are known. Specific examples include but are not limited to: Re-based catalysts such as: [≡Sio—Re (≡CH'Bu)(CH$_2$'Bu)] (Copéret, C. *New J. Chem.* 2004, 28. 1-10; Thieuleux, C.; Copéret, C.; Dufaud, V.; Marangelli, C.; Kuntz, E.; Basset, J. M. *J. Mol. Catal. A: Chemical* 2004, 213, 47-57; Chabanas, M.; Baudouin, A.; Coperet, C.; Basset, J. *J. Am. Chem. Soc.* 2001, 123, 2062); [Re(CO)$_3$OH]$_4$SiO$_2$ (Copéret, C. *New J. Chem.* 2004, 28. 1-10); Re$_2$O$_7$/mesoporous Al$_2$O$_3$ (Balcar, H.; Hamtil, R.; Zilkova, N.; Cejka, *J. Catal. Lett.* 2004, 97 (1-2), 25-29; Oikawa, T.; Ookoshi, T.; Tanaka, T.; Yamamoto, T.; Onaka, M. *Microporous and Mesoporous Materials* 2004, 74, 93-103); Re$_2$(CO)$_{10}$/Al$_2$O$_3$ (Mol, J. C.; Moulijn, J. A. *Adv. Catal.* 1975, 24, 131); Re$_2$O$_7$/Al$_2$O$_3$ (Mol, J. C.; Moulijn, J. A. *Adv. Catal.* 1975, 24, 131; Grubbs, R. H. Alkene and Alkyne Metathesis Reactions. In *Comprehensive Organometallic Chemistry*; Wilkinson, G., Ed. Pergamon Press Ltd.: New York, 1982; p 499; Mol, J. C.; Visser, F. R.; Boelhouwer, C. *J. Catal.* 1970, 17, 114; Satio, K.; Yamaguchi, T.; Tanabe, K. *Bull. Chem. Soc. Jpn.* 1979, 52, 3192); Re$_2$O$_7$/Al$_2$O$_3$/SiO$_2$ (Mol, J. C. *Catal. Today* 1999, 289-299); Re$_2$O$_7$/Al$_2$O$_3$/Mt$_x$O$_y$ (Mt=transition metal) (Nakamura, R.; Echigoya, E. *Chem. Lett.* 1977, 10, 1227); Re$_2$O$_7$/zeolite (Hamdan, H.; Ramli, Z. *Studies in Surface Science and Catalysis* 1997, 957); Re$_2$O$_7$/Al$_2$O$_3$/SnR$_4$ (R=Me, Et, Bu) (Mol, J. C. *Catal. Today* 1999, 289-299; Finkel'shtein, E. Sh.; Ushakov, N. V.; Portnykh, E. B. *J. Mol. Catal.* 1992, 76, 133); CH$_3$ReO$_3$/Al$_2$O$_3$/SiO$_2$ (Hermann, W. A.; Wagner, W.; Flessner, U. N.; Volkhardt, U.; Komber, H. *Angew. Chem. Int. Ed. Eng.* 1991, 30(12), 1636-1638; Mathew, T. M.; du Plessis, J. A. K.; Prinsloo, J. J. *J. Mol. Catal.* 1999, 148, 157); and ReO$_3$/SiO$_2$ (Tsuda, N.; Fujimori, A. *J. Catal.* 1981, 69, 410); Mo-based catalysts such as: MoO$_3$/HMS (HMS=hexagonal mesoporous silica) (Ookoshi, T.; Onaka, M. *Chem. Commun.* 1998, 2399-2400); MoO$_3$/SiO$_2$ (*Olefin Metathesis and Metathesis Polymerization*; Ivin, K. J., Mol, J. C., Eds.; 2$^{nd}$ ed., 1996, p 496); MoO$_3$/Al$_2$O$_3$ (*Olefin Metathesis and Metathesis Polymerization*; Ivin, K. J., Mol, J. C., Eds.; 2$^{nd}$ ed., 1996, p 496; Thomas, R.; Moulijn, J. A. *J. Mol. Catal.* 1982, 15, 157; Gruenert, W.; Stakheev, A. Yu.; Feldhaus, R; Anders, K; Shpiro, E. S.; Minachev, Kh. M. *J. Catal.* 1992, 135, 287; Coperet, C. *New J. Chem.* 2004, 28. 1-10); MoO$_3$/Al$_2$O$_3$/Sn (CH$_3$)$_4$ (Handzlik, J.; Ogonowski, J. *Catal. Lett.* 2002, 83, 287); MoO$_x$/β-TiO$_2$ (Tanaka, K.; Miyahara, K. *Chem. Commun.* 1980, 666); MoO$_3$/TiO$_2$/SnMe$_4$ (Pariya, C.; Jayaprakash, K. N.; Sarkar, A. *Coord. Chem. Rev.* 1998, 168, 1-48); MoO$_3$/CoO/Al$_2$O$_3$ (Grubbs, R. H.; Swetnick, S. J. *J. Mol. Catal.* 1980, 8, 25; Turner, L.; Howman, E. J.; Bradshaw, C. P. C. *J. Catal.* 1967, 7, 269; Alkema, H. J.; Van Helden, R. *Chem. Abstr.* 1968, 69, 95906; Mol, J. C.; Moulijn, J. A. *Adv. Catal.* 1975, 24, 131; Grubbs, R. H. Alkene and Alkyne Metathesis Reactions. In *Comprehensive Organometallic Chemistry*; Wilkinson, G., Ed. Pergamon Press Ltd.: New York, 1982; p 499); MoO$_3$/Cr$_2$O$_3$/Al$_2$O$_3$ (Mol, J. C.; Moulijn, J. A. *Adv. Catal.* 1975, 24, 131); Mo(CO)$_6$/SiO$_2$ (Brenner, A.; Hucul, D. A.; Hardwick, S. J. *Inorg. Chem.* 1979, 18, 1478); Mo(CO)$_6$/γ-Al$_2$O$_3$ (Olsthoorn, A. A.; Moulijn, J. A. *J. Mol. Catal.* 1980, 8, 147; Farona, M. F.; Tucker, R. L. *J. Mol. Catal.* 1980, 8, 25; Mol, J. C.; Moulijn, J. A. *Adv. Catal.* 1975, 24, 131); (π-C$_3$H$_5$)$_4$Mo/SiO$_2$/Al$_2$O$_3$ (Yermakov, Y. I.; Kuznetzov, B. N.; Grabovski, Y. P.; Startzev, A. N.; Lazutkin, A. M.; Zakharov, V. A.; Lazutkina, A. I. *J. Mol. Catal.* 1976, 1, 93); (π-C$_3$H$_5$)$_4$Mo/Al$_2$O$_3$ (Iwasawa, Y.; Ogasawara, S.; Soma, M. *Chem. Lett.* 1978, 1039); [≡SiO—Mo(≡C'Bu)(CH$_2$'Bu)$_2$] (Copéret, C. *New J. Chem.* 2004, 28. 1-10); [≡SiO—Mo(≡NH)(≡CH'Bu)(CH$_2$'Bu)] (Copéret, C. *New J. Chem.* 2004, 28. 1-10); Mo(CHCMe$_2$Ph)(N-2,6-$^i$Pr$_2$C$_6$H$_3$)[OCMe(CF$_3$)$_2$]$_2$/MCM-41 (Balcar, H.; Zilkova, N.; Sedlacek, J.; Zednik, J. *J. Mol. Catal.* 2005, 232, 53); and MoCl$_x$/PbMe$_4$/ SiCl$_4$ (Bykov, V. I.; Butenko, T. A.; Finkel'shtein, E. Sh. Pat. SU 1664786); W-based catalysts such as WO$_3$/SiO$_2$ (Schubert, M.; Gerlach, T.; Hesse, M.; Stephan, J.; Bohm, V.; Brodhagen, A.; Poplow, F. Pat. U.S 2004260135); WO$_3$/Al$_2$O$_3$ (De Vries, J. L. K. F.; Pott, G. T. Rec. *Trav. Chim. Pays-Bas* 1977, 96, M115); WO$_3$/Al$_2$O$_3$/HY zeolite (Huang, S.; Liu, S.; Xin, W.; Bai, J.; Xie, S.; Wang, Q.; Xu, L. *J. Mol. Catal. A: Chemical* 2005, 226, 61-68); (π-C$_4$H$_7$)$_4$W/SiO$_2$ (Startsev A. N.; Kuznetsov, b. N.; Yermakov, Y. I. *React. Kinet. Catal. Lett.* 1976, 3, 321); WO$_3$/SiO$_2$/MgO (Mazurek, H.; Sofranko, J. A. Pat. U.S. Pat. No. 4,788,376); WO$_3$/ZrO$_2$ (Yoshinaga, Y.; Kudo, M.; Hasegawa, S.; Okuhara, T. *Applied Surface Science* 1997, 121/122 339); H$_3$PW$_{12}$O$_{40}$ (Hudec, P.; Prandova, K. *Collection of Czechoslovak Chemical Communications* 1995, 60(3), 443); (Polystyrylbipyridine) W(CO)$_4$ (Tamagaki, S.; Card, R. J.; Neckers, D.C. *J. Am. Chem. Soc.* 1978, 100, 6635-6639); [≡Sio—W(CH'Bu)(CH$_2$'Bu)$_2$] (Copéret, C. New J. Chem. 2004, 28. 1-10); ('BuO)$_2$W=C'Bu]/SiO$_2$ (Weiss, K.; Lössel, G. *Angew. Chem. Int. Ed. Eng.* 1982, 28(1), 62-64); [(neopentyl)$_2$W=C'Bu]/SiO$_2$ (Weiss, K.; Lössel, G. *Angew. Chem. Int. Ed. Eng.* 1982, 28(1), 62-64); [Cl$_2$W=C'Bu]/SiO$_2$ (Weiss, K.; Lössel, G. *Angew. Chem. Int. Ed. Eng.* 1982, 28(1), 62-64); WCl$_6$/SiO$_2$/1,1,3,3-(CH$_3$)$_4$-disilacyclobutane (Shouvalova, O. V.; Bespalova, N. B.; Nieczypor, P.; Mol, J. C. NATO Science Series, II: Mathematics, Physics and Chemistry (2003), 122 (Novel Metathesis Chemistry), 173); Aryloxy tungsten/NbO$_x$/SiO$_2$/$^i$BuAlCl$_2$ (Verpoort, F.; Bossuyt, A.; Verdonck, L. *Chem. Commun.* 1996, 417); Schrock W carbene/SiO$_2$ (Weiss, K.; Hoffmann, K. *Mathematical and Physical Sciences* 1989 355); [Ru(polymer-CH$_2$OCOCF$_2$CF$_2$CF$_2$COO) (CF$_3$CO$_2$)(=CH-o-$^i$PrOC$_6$H$_4$)(IMesH$_2$) (Krause, Jens O.; Nuyken, Oskar; Wurst, Klaus; Buchmeiser, Michael R. *Chem. Eur. J.* 2004, 10, 777); and a solid-supported phosphine-free ruthenium alkylidene (Connon, S. J.; Blechert, S. *Bioorganic & Medicinal Chemistry Letters* 2002, 12(14) 1873).

In some embodiments Schrock catalysts are preferred as metathesis catalysts. See, e.g., U.S. Pat. Nos. 6,852,900; 6,660,813; 6,538,131; 6,380,420; and 5,942,638.

In some embodiments, Grubb catalysts are less preferred as metathesis catalysts.

In some embodiments, the metathesis catalyst is at least one of, or a mixture of, molybdic acid, ruthenium trichloride, ruthenium trichloride trihydrate, ruthenium tribromide, ruthenium triiodide, tungsten hexachloride, tungsten hexabromide, tungsten hexaiodide, molybdenum chloride, molybdenum bromide, molybdenum iodide, ruthenium oxide, tungsten oxide, tantalum chloride, tantalum bromide, tantalum iodide, tantalum oxide, a tetraalkyl or tetraaryltin complex of a tungsten halide, molybdenum halide, tantalum halide, rhenium halide, ruthenium halide, molybdenum oxide such as a lithium aluminum hydryde activated molybdenum oxide, rhenium oxide, cobalt oxide include cobalt oxide-molybdenum oxide, rhenium pentachloride, rhenium pentabromide, rhenium pentaiodide, trialkyl aluminum and dialkyl aluminum chloride complexes of rhodium halides, tungsten halide, molybdenum halide, ruthenium halide. See, e.g., U.S. Pat. No. 5,324,616; see also U.S. Pat. Nos. 6,727,396 and 5,672,803.

In some embodiments, such metal catalysts that are free of or do not incorporate organic ligands are preferred.

Particularly preferred olefin metathesis catalysts include, but are not limited to Schrock catalysts, molybdenum catalysts, tungsten oxide catalysts, and rhenium oxide catalysts, which are preferably on a solid support as discussed below.

4. Dual catalyst systems and methods. The present invention is carried out by reacting at least one first alkane as described above in the presence of (i) a first hydrogen transfer catalyst as described above and (ii) a second metathesis catalyst as described above, to produce the mixture of at least one lower molecular weight alkane and at least one higher molecular weight alkane. The conditions of the reaction are not critical, but in general the reacting step is carried out at an elevated temperature (e.g., 50, 100, or 150° C., up to 200, 250 or 300° C., or more, but in some embodiments with a temperature not greater than 300, 250, or 200° C.), for a time of one, five or ten minutes up to one or two hours or more, at atmospheric pressure or an elevated pressure. The reaction may be carried out continuously or as a batch reaction depending upon reactor design, all of which can be implemented in accordance with known techniques. The reaction may be a homogeneous reaction (that is, the catalysts free of a support) or a heterogeneous reaction (that is, the catalysts coupled to or immobilized on a solid support), again in accordance with known techniques.

The first alkane may, in some embodiments, be a linear or branched compound of the formula $C_nH_{2n+2}$ where n is 3-10. The at least one high molecular weight alkane may be a linear or branched compound of the formula $C_mH_{2m+2}$, where m is an integer from 4 to 40.

In other embodiments the first alkane is of a still higher molecular weight (e.g., a Fischer Tropsch wax). In such embodiments the lower molecular weight reaction products can be utilized as a "high molecular weight" alkane in a fuel, and the still higher molecular weight products recycled or subjected to cracking or other suitable reaction.

In some embodiments the first alkane is supplied to the reaction in the form of liquid a Fischer-Tropsch reaction product or a portion thereof. In such embodiments the at least one first alkane is linear, and the alkane is included in a mixed composition comprising both alkanes and alkenes, with the ratio of alkanes to alkenes being relatively high, for example a weight ratio of at least 10:1, 50:1, 100:1 or 200:1 or more.

The reaction is in some embodiments initiated by inclusion or addition of a hydrogen acceptor: that is, is carried out in the presence of a hydrogen acceptor. In some embodiments, the amount of the hydrogen acceptor is preferably not so great as to deleteriously bind to the catalyst and slow the reaction. In such embodiments, the molar ratio of the hydrogen acceptor to said hydrogen transfer catalyst is preferably not greater than 10:1. In some embodiments the catalyst itself may serve as a hydrogen acceptor, e.g., in the case of iridium catalysts such as (PCP)IrPhH, or complexes like (pincer)Ir(ethylene) (where "pincer" refers to polydentate ligands of the type illustrated in the references cited in section 2 above, or other such ligands known in the art).

When included, any suitable hydrogen acceptor can be used. In some embodiments olefin hydrogen acceptors are preferred. Examples of hydrogen acceptors include but are not limited to norbornene, t-butylethylene, ethylene, propene, $CH_2=CH(CH_2)_nCH_3$ where n is 1 to 25, etc. Note that the hydrogen acceptor may be exogenously added to the system or inherent in the composition being subject to the reaction (e.g., olefins may already be present in the product of a Fischer-Tropsch reaction).

Where one or the other, or both, catalysts are coupled to or immobilized on a solid support, the support may be porous or nonporous, in any suitable form, and formed from any suitable material such as alumina, silica, titania, kieselguhr, diatomaceous earth, bentonite, clay, zirconia, magnesia, zeolites, carbon black, activated carbon, graphite, fluoridated carbon, organic polymers, metals, metal alloys, and combinations thereof, in accordance with known techniques. See, e.g., U.S. Pat. No. 6,908,873.

Catalysts including iridium pincer catalysts can be immobilized in accordance with known techniques, with one example of an immobilized iridium pincer catalyst complex being represented by Formula (II):

wherein:

each R is independently H or a $C_1$-$C_{30}$ hydrocarbyl radical;

each $R_1$ is independently a $C_1$-$C_{30}$ hydrocarbyl radical;

each X is independently selected from O and $CH_2$;

L is any suitable linking group, including aromatic, aliphatic and mixed aromatic and aliphatic linking groups; and S is a solid support such as described above or below.

Catalysts can be immobilized by covalent coupling to a grafted or functionalized polystyrene support (e.g. Wang resin, Argogel resin, Merrifield resin, Tentagel resin, etc.) in accordance with known techniques. See, e.g., U.S. Pat. No. 6,951,958.

Catalysts can be immobilized by covalent coupling through a silicon or siloxane containing-linker to any suitable solid support, such as silica, in accordance with known techniques.

Catalysts can be immobilized by Lewis acid:Lewis base interactions, or binding to any suitable solid support, such as alumina, without covalent coupling, in accordance with known techniques.

In some embodiments, the production of branched higher molecular weight alkanes is advantageously minimized, such that at least one higher molecular weight alkane produced by the reaction comprises a mixture at a Molar ratio of linear alkanes to branched alkanes of at least 500:1, and more preferably at a Molar ratio of at least 1000:1.

In some embodiments, wherein the hydrogen transfer catalyst is immobilized on a solid support and the reaction is carried out in a solvent, the method may further comprise the step of separating free hydrogen transfer catalyst from said solvent. Such separating may be carried out by any suitable means, such as by adding an additional an adsorption agent to the solvent to adsorb otherwise free hydrogen transfer catalyst. Any suitable adsorption agent may be used, including but not limited to alumina, silica, titania, kieselguhr, diatomaceous earth, bentonite, clay, zirconia, magnesia, zeolites, carbon black, activated carbon, graphite, fluoridated carbon, organic polymers, metals, metal alloys, and combinations thereof. Without wishing to be bound to any particular theory, it is believed that the added free support adsorb otherwise free hydrogen transfer catalyst that would otherwise interfere with the activity of the (preferably also immobilized) metathesis catalyst.

One embodiment of the method of the present invention is schematically illustrated in Scheme 1 below, with an iridium catalyst as the hydrogen transfer catalyst.

Scheme 1

5. Additional process steps, apparatus and utility. Lower and higher molecular weight alkanes, particularly higher molecular weight liquid alkanes, produced by the methods of the present invention can be utilized as fuels and solvents in accordance with known techniques, and/or further processed by known techniques to produce fuels therefrom. For example, the higher molecular weight alkanes can be separated from the lower molecular weight alkanes by distillation, the higher molecular weight alkanes utilized as fuels, and the lower molecular weight alkanes utilized per se or returned and recycled for further synthesis. Additional processing techniques such as reforming, blending with other hydrocarbons or other refinery streams, and/or the addition of additives (e.g., oxygenates such as MTBE, ethanol, ETBE, etc; fuel adjuncts such as ignition improvers, stability improvers, corrosion inhibitors, detergent additives, cold flow improvers, combustion improvers, luminosity reducers/radiation quenchers, antimicrobial/antifungal adjuncts, antistats, and other conventional jet fuel adjuncts and mixtures thereof), to produce liquid hydrocarbon fuels such as gasoline (or "petrol") or diesel fuel, can also be carried out if desired, all in accordance with known techniques. See, e.g., U.S. Pat. Nos. 6,896,708 and 6,880,635; see also U.S. Pat. Nos. 6,884,916; 6,881,235; 6,863,802; 6,858,047; 6,767,372; 6,565,617; 6,551,502; 6,533,924; 6,527,816; 6,540,797; 6,890,364; and 6,833,064.

Figure 1:
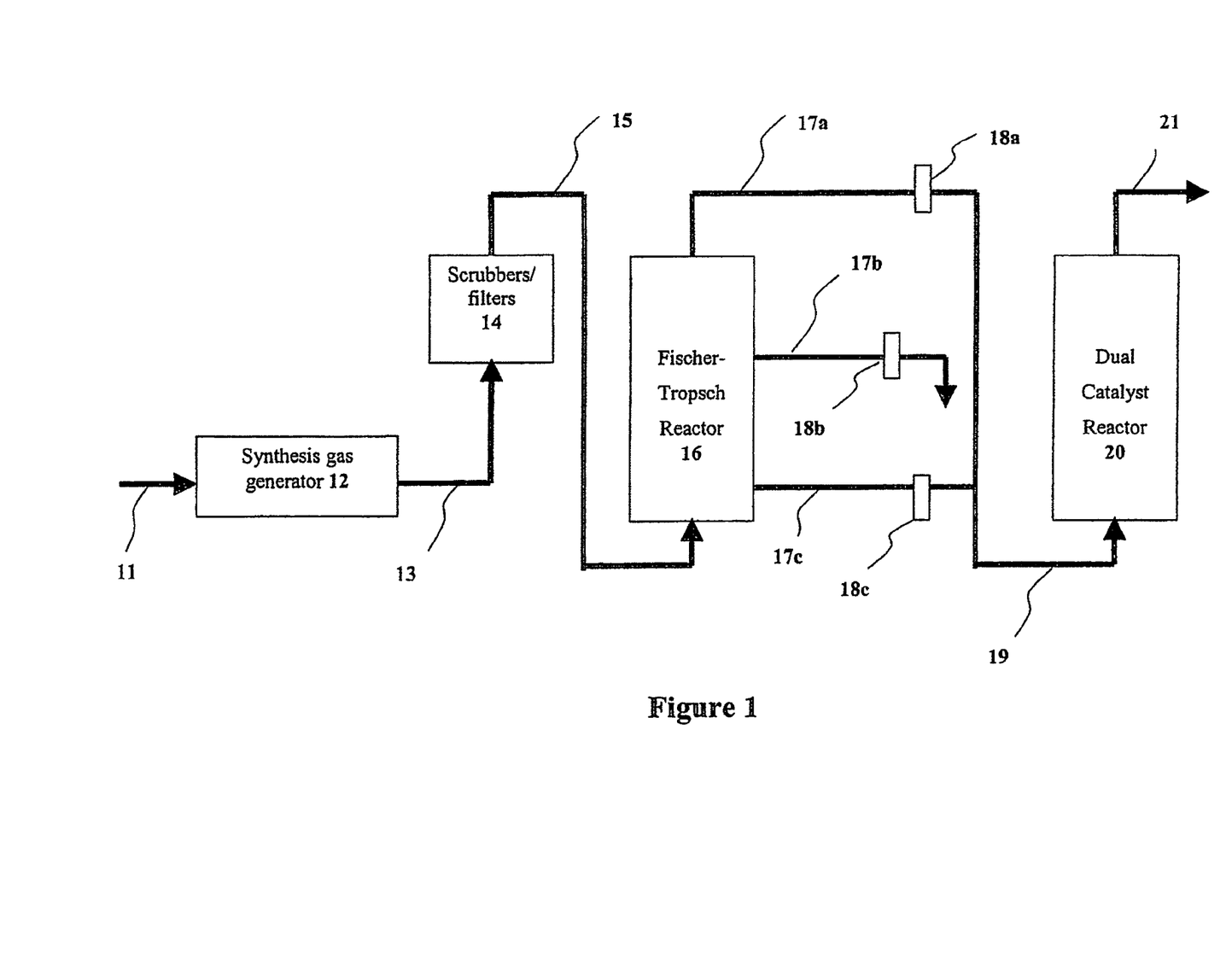

An apparatus for carrying out a method of the invention is schematically illustrated in FIG. 1. Carbonaceous or organic material such as coal, methane, natural gas, or biomass is supplied via line 11 to the synthesis gas generator 12, where it is partially oxidized by air, pure oxygen, steam and/or methane to produce synthesis gas, all of which may be carried out in accordance with known techniques. The synthesis gas exits generator 12 by line 13, and is then (optionally but preferably) at least partially cleaned of undesired compounds such as HCN, $NH_3$ and/or sulfur gases by scrubbers and/or filters 14. Any suitable scrubber, filter, or cleaning system may be utilized. See, e.g., U.S. Pat. Nos. 2,863,527; 4,088,735; 4,155,985; 3,975,178; 3,956,460; 4,007,129; 4,058,376; 4,189,307; and 4,271,133.

Synthesis gas exits the optional filters and/or scrubbers 14 by line 15 and enters Fischer-Tropsch reactor 16. Any suitable Fischer-Tropsch reactor may be utilized including slurry and non-slurry (fixed bed or fluidized bed) reactors (e.g., circulating fluidized bed reactors, ebulating or fixed fluidized bed reactors, slurry-phase bubbling bed reactors or slurry bubble-column reactors, etc.). The reactors can contain any suitable Fischer-Tropsch catalyst. Particular examples of suitable reactors and catalysts are set forth above and in the patents cited above and incorporated herein by reference. One or more feed lines 17a, 17B, and 17C containing the reaction product of the Fischer-Tropsch reaction leaves the reactor (e.g., the light fraction via line 17a, the medium fraction via line 17b, and the heavy fraction such as wax via line 17c). Each feed line 17a-17c may be controlled by a valve 18a-18c, and hence provides for controlled input to dual catalyst reactor 20 via line 19. (Alternatively, lines 17a-17c or any combination thereof may proceed directly to reactor 20 rather than feed through a common line 19).

For example, a medium molecular weight fraction of the Fischer-Tropsch reactor may be withdrawn via line 18b and the dual catalyst reactor 20 may be supplied with either: a light weight fraction of the F-T reaction via line 17a and valve 18a; a heavy weight or wax fraction of the F-T reaction via line 17c and valve 18c; or a mixture of light and heavy weight fractions in any suitable proportion via a combination thereof.

The dual catalyst reactor 20 may be of any suitable format or configuration, such as those described in connection with the Fischer-Tropsch reactor above. Product of the dual catalyst reaction is then taken by line 21 for use as a fuel, or for any other suitable purpose.

It will be appreciated that the apparatus of FIG. 1 is presented in schematic form. Additional components such as return lines for recycling output from a reactor for further reaction, separation or distillation units for separating the components of a reaction product for further processing, additional feed lines for adding or blending additional components or additives, etc., can also be included, as will be apparent to those skilled in the art. Lines can be consolidated or valves replaced or repositioned, separation can be achieved by distillation rather than fractionation, etc.

The dual catalyst reactions described herein convert a first alkane to alkanes of both higher and lower molecular weight ("higher" and "lower" being relative to the first alkane). In the fuel synthesis methods described above it is generally suggested that the higher molecular weight products of the dual catalyst reaction are desired. However, Fischer-Tropsch reactions also produce a wax product of still higher molecular weight, and when such waxes are further processed by the reactions of the invention, it is the lower molecular weight products utilized to make fuels and the higher molecular weight products utilized for recycling (or other purposes).

Thus the present invention also provides a method of making a liquid hydrocarbon fuel, such as diesel fuel or gasoline, from a synthesis gas by the Fischer-Tropsch reaction, wherein said fuel comprises at least one high molecular weight alkane, wherein at least a portion of the product of said Fischer Tropsch reaction comprises a wax, and wherein said wax is of still higher molecular weight than said high molecular weight alkane, in which at least a portion of said wax is converted to said at least one high molecular weight alkane by reacting said wax in the presence of a dual catalyst system comprising: (i) a hydrogen transfer catalyst and (ii) a metathesis catalyst to produce said at least one high molecular weight alkane (here the "high molecular weight alkane" is the lower molecular weight product of the dual catalyst reaction).

Note that very low molecular weight alkanes produced from the F-T reaction can also be supplied to the dual catalyst system to aid in the production of the lower molecular weight alkanes (or "medium" molecular weight alkanes, relative to the very low molecular weight alkanes) from the high molecular weight waxes.

Apparatus as described in FIG. 1 above can be modified to carry out such methods by configuring them to draw the wax product from the Fischer Tropsch reactor 16 to the dual catalyst reactor 18.

Figure 2:
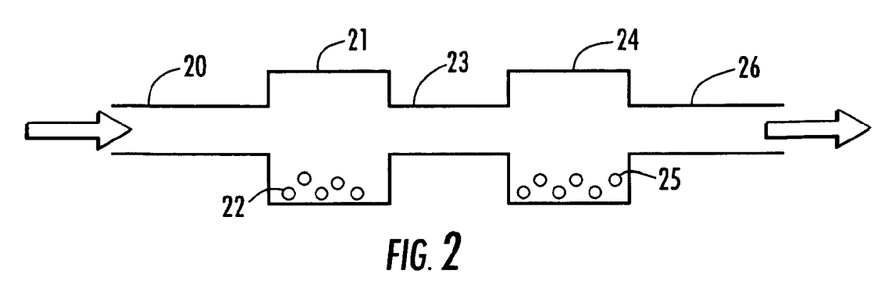
FIG. 2 is a schematic illustration of a dual catalyst reactor of the present invention, in which the two catalysts are separated from one another.
Figure 3:
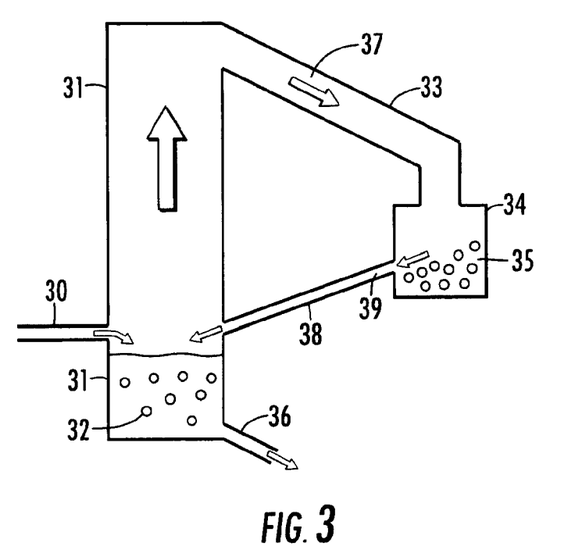
FIG. 3 is a schematic illustration of a dual catalyst reactor of the present invention, again in which the two catalysts are separated from one another.

Particular examples of dual catalyst reactors in which the catalysts are separated rather than contained together, are shown in FIGS. 2-3.

In FIG. 2, an inlet 20 for alkane is provided to a first reaction chamber 21 which contains immobilized hydrogen transfer catalyst 22. A connecting line 23 provides fluid communication between the first reaction chamber and a second reaction chamber 24 which contains immobilized metathesis catalyst 25. An outlet line 26 permits removal of alkane reaction product from the second chamber. Alkane can pass from the chambers in liquid or gas form.

In FIG. 3, an inlet 30 for liquid alkane is provided to a first reaction chamber 31 which contains immobilized hydrogen transfer catalyst 32. Alkane reaction product leaves as a gas or vapor to connecting line 33, which provides fluid communication between the first reaction chamber and a second reaction chamber 34, which contains immobilized metathesis catalyst 35. Connecting line 33 is configured to distill vapor products volatilized from the first reaction chamber into the second reaction chamber (e.g., by appropriate geometric positioning, provision of an insulated jacket, 37 provision of a cooling system, etc.). Liquid reaction product from the second reaction chamber can be removed, or returned if desired by outlet line/return line 38. Alkane product can exit, typically as a liquid, through outlet line 36 connected to reaction chamber 31 (but which could alternatively be connected to reaction chamber 34).

Immobilization of the catalyst in devices such as shown in FIGS. 2-3 can be achieved by any suitable means or combination of means, including coupling to a solid support, physical or gravity trapping in a well, retention within a chamber by a filter, frit, screen or the like 39, etc.

Devices of FIGS. 2-3 can be utilized where different temperatures for the two reactions are desired. Such apparatus, or variations thereof that will be apparent to persons skilled in the art, are useful when it is desired to carry out the different reactions at different temperatures (e.g., 120 or 150° C., up to 250° C., for the dehydrogenation reaction; 30, 40 or 50° C., up to 100° C., for the metathesis reaction).

6. Tandem catalyst systems. In some embodiments of the foregoing, including both those concerning immobilized or supported catalysts and those concerning non-immobilized or unsupported catalysts, the hydrogen transfer catalyst (e.g., the iridium pincer complex catalyst) comprises at least two different hydrogen transfer catalysts in combination (e.g., at least two different iridium pincer complex catalysts in combination). For example, hydrogen transfer catalyst may comprise: (a) a pair of catalysts of Formula I or Formula II, wherein in one member of the pair each X is O and in the other member of the pair each X is $CH_2$; (b) a pair of catalysts of Formula I or Formula II, wherein in one member of the pair at least one R group is different from that found in the same position of the other member of the pair; (c) a pair of catalysts of Formula I or Formula II, wherein in one member of the pair at least one $R_1$ group is different from that found in the same position of the other member of the pair; and (d) combinations of the foregoing. In some embodiments, the use of a combination of two different hydrogen transfer catalysts gives better selectivity for the conversion of two equivalents of a $C_n$ hydrocarbon to one equivalent of a $C_{2n-2}$ hydrocarbon (plus ethane).

While the present invention has been described with reference to single alkanes such as "first alkane", "low molecular weight alkane", "high molecular weight alkane" "wax", and alkanes of particular chain lengths, it will be appreciated that in most embodiments of the invention the product alkanes, and in many embodiments the reactant alkanes represent a distribution of multiple alkanes of different carbon number (the majority of which may be within the range indicated) rather than a single compound. Thus, where an alkane is identified by a chain length or range of chain lengths herein, the alkane may be treated (for the purpose of the instant description) as: (i) a single alkane of the identified chain length (alone or in combination with others), or (ii) a mixture of multiple alkanes having either a mean or median chain length corresponding to the identified chain length.

The present invention is described in the following non-limiting examples.

EXAMPLES 1-10

Examples of Supported Ir Pincer Complexes for Transfer Dehydrogenation

Example 1

Synthesis of {4-O($CH_2$)$_3$Si(OMe)$_3$-$C_6H_2$-2,6-[OP(t-Bu)$_2$]$_2$}Ir($C_2H_4$)

{4-OK—$C_6H_2$-2,6-[OP(t-Bu)$_2$]$_2$}Ir($C_2H_4$) (27 mg, 0.04 mmol) was added into a ethylene saturated tetrahydrofuran (2 mL) solution of I($CH_2$)$_3$Si(OMe)$_3$ (50 mg, 0.17 mmol) in a dried Kontes Schlenk flask under an argon atmosphere. Ethylene was added into the flask at −78° C. after three freeze-pump-thaw cycles. The flask was sealed tightly with a TEFLON® plug, and the solution stirred in a 65° C. oil bath for 2 hours. NaO-t-Bu (19 mg, 0.19 mmol) was weighed into the flask, and the solution stirred at room temperature overnight. Volatiles were evaporated under vacuum, pentane (10 mL) was added into the flask via syringe. The solution was cannula-filtered through a pad of CELITE®, volatiles were evaporated under vacuum, and the resulting red solid was dried under vacuum overnight to give 27 mg (77% yield) of pure product. $^1$H NMR($C_6D_6$): δ 0.73-0.76 (m, 2H), 1.27 (t, J=6.8 Hz, 36H), 1.84-1.90 (m, 2H), 3.14 (t, J=2.4 Hz, 4H), 3.41 (s, 9H), 3.71 (t, J=6.4 Hz, 2H), 6.65 (s, 2H). $^{31}$P {$^1$H} NMR($C_6D_6$): δ 181.4 (s).

Example 2

Synthesis of {4-O($CH_2$)$_3$Si(Me)$_2$(OMe)—$C_6H_2$-2,6-[OP(t-Bu)$_2$]$_2$}Ir($C_2H_4$)

The same procedure described above was followed except that I($CH_2$)$_3$Si(OMe)$_3$ was replaced by I($CH_2$)$_3$Si(Me)$_2$ (OMe) (44 mg, 0.17 mmol), giving 23 mg (75% yield) of pure product. $^1$H NMR($C_6D_6$): δ0.02 (s, 6H), 0.55-0.60 (m, 2H), 1.27 (t, J=6.4 Hz, 36H), 1.66-1.73 (m, 2H), 3.14 (br, 4H), 3.23 (s, 3H), 3.71 (t, J=6.4 Hz, 2H), 6.68 (s, 2H). $^{31}$P {$^1$H} NMR ($C_6D_6$): δ181.5 (s).

Example 3

Synthesis of {4-O($CH_2$)$_3$Si(OMe)$_3$-$C_6H_2$-2,6-[OP(t-Bu)$_2$]$_2$}Ir(COE) Supported on Silica {4-O($CH_2$)$_3$Si(OMe)$_3$-$C_6H_2$-2,6-[OP(t-Bu)$_2$]$_2$}Ir($C_2H_4$) (24 mg, 0.03 mmol) and Grace Silica XPO 2402 (525 mg) were weighed into a Kontes Schlenk flask under an argon atmosphere. cis-cyclooctene (COE, 2.8 mL) was added via syringe, and the suspension stirred in a 160° C. oil bath for 2 days. (Me$_3$Si)NMe$_2$ (1 mL, 6 mmol) was added via syringe, and the suspension stirred at room temperature for 2 days. The orange solids were filtered and washed with tetrahydrofuran, toluene, and pentane, and was dried under vacuum to give 505 mg (92% yield) of product.

Example 4

Synthesis of {4-O($CH_2$)$_3$Si(Me)$_2$(OMe)—$C_6H_2$-2,6-[OP(t-Bu)$_2$]$_2$}Ir(COE) Supported on Silica The same procedure described above was followed except that {4-O($CH_2$)$_3$Si(OMe)$_3$-$C_6H_2$-2,6-[OP(t-Bu)$_2$]$_2$}Ir($C_2H_4$) was replaced by {4-O($CH_2$)$_3$Si(Me)$_2$(OMe)—$C_6H_2$-2,6-[OP(t-Bu)$_2$]$_2$}Ir($C_2H_4$) (23 mg, 0.03 mmol), giving 450 mg (82% yield) of product.

Example 5

Synthesis of Merrifield Resin-Supported POCOP Ir Ethylene Catalyst

Merrifield resin (Aldrich, 2% cross-linked, 200-400 mesh, 2.25 mmol Cl/g; 60 mg, 0.135 mmol of Cl), {4-OK—$C_6H_2$-2,6-[OP(t-Bu)$_2$]$_2$}Ir($C_2H_4$) (80 mg, 0.12 mmol), and KH (20 mg, 0.5 mmol) were weighed into a Kontes Schlenk flask under an argon atmosphere. Tetrahydrofuran (5 mL) was added into the flask via syringe. Ethylene was added into the flask at −78° C. after three freeze-pump-thaw cycles. The flask was sealed tightly with a TEFLON® plug, and the solution stirred in a 65° C. oil bath for 15 days. The solution was filtered, and the solids were washed with 5 mL of tetrahydrofuran six times. The resulting red beads then were added into a Kontes Schlenk flask. Tetrahydrofuran (5 mL) was added into the flask via syringe. Ethylene was added into the flask at −78° C. after three freeze-pump-thaw cycles. t-BuOH (74 mg, 1 mmol) was vacuum transferred into the flask, and the suspension stirred at room temperature for 2 hours. The solids were filtered and washed with 5 mL of H$_2$O three times. Volatiles were evaporated under vacuum. The resulting red beads were dried under vacuum overnight to give 60 mg (43% yield) of product.

Example 6

Transfer Dehydrogenation of Cyclooctane with Silica-Supported POCOP Ir Catalyst (SiO$_2$—POCOPIr)

A flask was charged with 35 mg (1.9 μmol of Ir) of silica-supported POCOP Ir catalyst (prepared by the procedure describe in Example 4), 0.45 mL (3.48 mmol) of tert-butyl ethylene as hydrogen acceptor, 0.59 mL (4.39 mmol) of cyclooctane. The flask was sealed tightly with a TEFLON® plug under an argon atmosphere, and the solution stirred in a 200° C. oil bath. Periodically, the flask was removed from the oil bath and cooled, an aliquot was removed from the flask, and analyzed by GC and NMR spectroscopies. The turnover number is 794 after 15 hours and 793 after 39 hours.

Example 7

Transfer Dehydrogenation of Cyclooctane with Merrifield Resin-Supported POCOP Ir Catalyst (Merrifield-POCOPIr)

Merrifield resin-supported POCOP Ir catalyst (6 mg) was weighed into a J-Young NMR tube. Mesitylene-d$_{12}$ (0.4 mL), tert-butyl ethylene (10 μL, 77.6 μmol) and cyclooctane (10 μL, 74.5 μmol) were added into the tube via syringe. The NMR tube was sealed tightly with a TEFLON® plug under an argon atmosphere, and inserted into a 180° C. oil bath. Periodically, the NMR tube was removed from the flask, and analyzed by NMR spectroscopy. After 2 days, the conversion of tert-butyl ethylene into 2,2'-dimethyl butane was 80%. The catalyst was then filtered, washed with 1 mL of pentane three times, and dried under vacuum overnight. The recycled catalyst was tested for transfer dehydrogenation of cyclooctane following the same produce described above. After 2 days, the conversion of tert-butyl ethylene into 2,2'-dimethyl butane was 20%. The catalyst was then recycled again and tested for transfer dehydrogenation of cyclooctane. After 2 days, no tert-butyl ethylene was converted into 2,2'-dimethyl butane.

Example 8

Transfer Dehydrogenation of Cyclooctane with Alumina-Supported {4-OK—$C_6H_2$-2,6-[OP(t-Bu)$_2$]$_2$}Ir($C_2H_4$) catalyst (OK—Ir/Al$_2$O$_3$)

{4-OK—$C_6H_2$-2,6-[OP(t-Bu)$_2$]$_2$}Ir($C_2H_4$) (1.7 mg, 2.5 μmol) and cyclooctane (850 mg, 7.58 mmol) were weighed into a Kontes Schlenk flask under an argon atmosphere, and the solution stirred at room temperature until all solids dissolved. γ-alumina (280 mg, 2.7 mmol; previously calcined at 550° C.) was weighed into the flask, and the suspension stirred at room temperature. When the solution became colorless, tert-butyl ethylene (638 mg, 7.59 mmol) was weighed into the flask. The flask was sealed tightly with a TEFLON® plug under an argon atmosphere, and the suspension stirred in a 200° C. oil bath. Periodically, the flask was removed from the oil bath and cooled; an aliquot was removed from the flask, and analyzed by GC and NMR spectroscopies. After 2398 minutes, the catalyst was filtered and washed with 1.5 mL of cyclooctane four times. Fresh cyclooctane (850 mg, 7.58 mmol) and tert-butyl ethylene (638 mg, 7.59 mmol) was added into a flask which contained the recycled catalyst, and the suspension stirred in a 200° C. oil bath. Periodically, the flask was removed from the oil bath and cooled; an aliquot was removed from the flask, and analyzed by GC and NMR spectroscopies. After another 2398 minutes, the catalyst was recycled again for a new transfer dehydrogenation reaction following the same procedure described above. Besides the formation of 2,2'-dimethyl-butane (TBA) through the hydrogen transfer reaction, 2,3-dimethyl-2-butene (DM2B) and 2,3-dimethyl-1-butene (DM1B) were observed as the isomerization products of tert-butyl ethylene in GC and NMR spectra. Data are given in the Table below.

Equivalents of hydrogen transfer product TBA, and isomerization products of tert-butyl ethylene, DM2B and DM1B.

|  | OK—Ir/Al₂O₃ | | | OK—Ir/Al₂O₃ 1st[a] | | | OK—Ir/Al₂O₃ 2nd[b] | | |
| --- | --- | --- | --- | --- | --- | --- | --- | --- | --- |
| Time | TBA | DM2B | DM1B | TBA | DM2B | DM1B | TBA | DM2B | DM1B |
| 8 min | 405 | 178 | / | | | | | | |
| 31 min | 945 | 326 | / | | | | | | |
| 178 min | 1400 | 570 | / | | | | | | |
| 928 min | 1714 | 746 | 57 | 1047 | 907 | 105 | 1017 | 1690 | 377 |
| 2398 min | 2065 | 840 | 83 | 1289 | 1051 | 188 | 1276 | 1270 | 595 |

[a]Data for the first recycled catalyst.
[b]Data for the second recycled catalyst.

Examples 9 and 10

A Comparison of Transfer Dehydrogenation Activity of Heterogeneous and Homogeneous PCP Ir Catalysts Example 9

Transfer Dehydrogenation of n-octane with Alumina-Supported {4-Me₂N—C₆H₂-2,6-[CH₂P(t-Bu)₂]₂}IrH₂ catalyst (NMe₂-Ir/Al₂O₃)

To 100 mg of γ-alumina and 3.1 mg (4.9 μmol, 5 mM) of {4-Me₂N—C₆H₂-2,6-[CH₂P(t-Bu)₂]₂}IrH₂, 1 mL n-octane (6.15 mmol) was added. The liquid phase was initially red in color but became clear while the solid phase acquired the red color. 70 μL of tert-butylethylene (0.54 mmol) was then added to the mixture which was heated at 125° C. while the reaction was monitored by GC. Throughout the course of the reaction time the alumina was orange or red in color and the solution was clear. Data are given in the Table below.

| Time (min) | 1-Octene (mM) | Total octene (mM) |
| --- | --- | --- |
| 5 | 0 | 5 |
| 10 | 1 | 10 |
| 15 | 2 | 15 |
| 30 | 3 | 30 |
| 60 | 3 | 59 |
| 120 | 4 | 99 |
| 240 | 4 | 130 |

When the same procedure as above was used but with basic alumina instead of γ-alumina, the reaction gave higher selectivity for 1-octene, but otherwise proceeded no differently. Data are given in the Table below.

| Time (min) | 1-Octene (mM) | Total octene (mM) |
| --- | --- | --- |
| 15 | 5 | 12 |
| 30 | 5 | 25 |
| 60 | 6 | 40 |
| 120 | 6 | 67 |
| 240 | 7 | 96 |

Example 10

Transfer Dehydrogenation of n-octane with Homogeneous {4-Me$_2$N—C$_6$H$_2$-2,6-[CH$_2$P(t-Bu)$_2$]$_2$}IrH$_2$ Catalyst (NMe$_2$-Ir)

tert-Butylethylene (70 μL, 0.54 mmol was added to a solution of 3.1 mg (4.9 μmol, 5 mM) of {4-Me$_2$N—C$_6$H$_2$-2,6-[CH$_2$P(t-Bu)$_2$]$_2$}IrH$_2$ in n-octane (1 mL, 6.15 mmol) and the solution was heated at 125° C. while the reaction was monitored by GC. Throughout the course of the reaction the solution was dark red. Data are given in the Table below.

| Time (min) | 1-Octene (mM) | Total octene (mM) |
|---|---|---|
| 5 | 2 | 3 |
| 10 | 3 | 5 |
| 15 | 4 | 7 |
| 30 | 9 | 22 |
| 60 | 15 | 43 |
| 120 | 16 | 73 |
| 240 | 16 | 98 | tubes, an upper tube and a lower tube. The upper tube is insulated and positioned so that vapors volatilized from heating of the contents of the lower flask are distilled therein and travel into the upper flask. Both tubes are connected to the lower flask at a position that provides a well in the bottom of the lower flask where immobilized dehydrogenation catalyst is trapped. The lower tube contains a frit at the mouth of the upper flask to retain immobilized metathesis catalyst in the upper flask, When the lower flask is heated by an external heat supply hydrocarbons distil through the upper tube and return through the lower tube. A stir bar is provided in the upper flask to agitate the contents thereof (e.g., the particle-immobilized catalyst).

Example 11

Alkane Metathesis with Separated Heterogeneous Catalyst: Ir Catalyst Supported Al$_2$O$_3$ (2.8 μmol Ir on 45 mg Al$_2$O$_3$)

The lower flask in the above Figure was charged with 46.8 mg (1.8 mg, 2.8 μmol of {4-OK—C$_6$H$_2$-2,6-[OP(t-Bu)$_2$]$_2$}Ir (C$_2$H$_4$) and 45 mg, 0.44 mmol of γ-Al$_2$O$_3$), 19.1 mg (118 μmol) of hexamethylbenzene, and 3 mL (18.4 mmol) of n-octane. The upper was charged with 310 mg (67 μmol) of Re$_2$O$_7$/Al$_2$O$_3$. The suspension in the lower flask stirred in a 220° C. oil bath, and the suspension in the upper flask stirred at 40 to 80° C. Periodically, the lower flask was removed from the oil bath and cooled; an aliquot was removed from the flask, and analyzed by GC. The catalysts were recycled two times for new alkane metathesis reactions. Data are given in the Table below.

| Time | C2/C3 | C4 | C5 | C6 | C7 | C9 | C10 | C11 | C12 | C13 | C14 | C>14 | Total TONs |
|---|---|---|---|---|---|---|---|---|---|---|---|---|---|
| 3 h | 1 | 2 | 4 | 9 | 14 | 17 | 13 | 9 | 5 | 1 | | | 75 |
| 31 h | 14 | 34 | 63 | 128 | 220 | 266 | 186 | 115 | 64 | 16 | 3 | | 1109 |
| 78 h | 56 | 151 | 255 | 405 | 519 | 420 | 326 | 255 | 131 | 30 | 9 | 3 | 2561 |
| 148 h | 92 | 158 | 234 | 410 | 564 | 485 | 397 | 319 | 219 | 84 | 27 | 15 | 2977 |
| 1st recycle, removed liquid, washed solids with 2 mL of octane four times | | | | | | | | | | | | | |
| 20 h | 22 | 39 | 49 | 79 | 103 | 101 | 73 | 51 | 30 | 12 | 4 | 1 | 563 |
| 50 h | 84 | 121 | 137 | 182 | 242 | 252 | 194 | 144 | 90 | 46 | 18 | 12 | 1526 |
| 101 h | 142 | 194 | 205 | 258 | 343 | 388 | 322 | 249 | 165 | 79 | 32 | 22 | 2399 |
| 2nd recycle, removed liquid, washed solids with 2 mL of octane four times | | | | | | | | | | | | | |
| 50 h | 19 | 26 | 26 | 36 | 59 | 70 | 57 | 40 | 22 | 9 | 3 | 1 | 368 |
| 101 h | 34 | 41 | 40 | 51 | 75 | 109 | 95 | 71 | 44 | 20 | 9 | 7 | 596 |

Examples 11 and 12

Procedures for Alkane Metathesis Reactions with Separated Heterogeneous Transfer Dehydrogenation and Olefin Metathesis Catalysts: {4-OK—C$_6$H$_2$-2,6-[OP(t-Bu)$_2$]$_2$}Ir(C$_2$H$_4$)/Al$_2$O$_3$ and Re$_2$O$_7$/Al$_2$O$_3$ A device was constructed which allows catalyst isolation and a method to heat each catalyst at different temperatures. The device contains two flasks with one positioned below the other. The lower flask is connected to the upper flask by two

Example 12

Alkane Metathesis with Separated Heterogeneous Catalyst: Ir Catalyst Supported Al$_2$O$_3$ (2.8 μmol Ir on 280 mg Al$_2$O$_3$)

The same procedure described above was followed except that 2.8 μmol of {4-OK—C$_6$H$_2$-2,6-[OP(t-Bu)$_2$]$_2$}Ir(C$_2$H$_4$) catalyst was supported by 280 mg (2.75 mmol) of γ-Al$_2$O$_3$. Data are given in the Table below.

| Time | C2/C3 | C4 | C5 | C6 | C7 | C9 | C10 | C11 | C12 | C13 | C14 | C > 14 | Total TONs |
|---|---|---|---|---|---|---|---|---|---|---|---|---|---|
| 18 h | 21 | 67 | 123 | 212 | 307 | 318 | 246 | 153 | 85 | 23 | 6 | 1 | 1562 |
| 52 h | 89 | 211 | 315 | 450 | 656 | 745 | 606 | 424 | 255 | 101 | 36 | 20 | 3908 |
| 1st recycle, removed liquid, washed solids with 2 mL of octane four times ||||||||||||||
| 18 h | 12 | 36 | 56 | 93 | 135 | 157 | 122 | 78 | 43 | 12 | 3 | 1 | 748 |
| 52 h | 32 | 77 | 101 | 153 | 225 | 269 | 227 | 157 | 89 | 26 | 7 | 3 | 1366 |
| 2nd recycle, removed liquid, washed solids with 2 mL of octane four times ||||||||||||||
| 18 h | 9 | 24 | 36 | 61 | 108 | 160 | 130 | 85 | 48 | 13 | | | 674 |

The foregoing is illustrative of the present invention, and is not to be construed as limiting thereof. The invention is defined by the following claims, with equivalents of the claims to be included therein.

That which is claimed is:

1. A method of converting at least one first alkane to a mixture of at least one lower molecular weight alkane and at least one higher molecular weight alkane, comprising:
reacting a first alkane in the presence of a dual catalyst system comprising: (i) a hydrogen transfer catalyst and (ii) a metathesis catalyst to produce said mixture of at least one low molecular weight alkane and at least one high molecular weight alkane, said reacting step carried out in the presence of a hydrogen acceptor, and wherein the molar ratio of said hydrogen acceptor to said hydrogen transfer catalyst is not greater than 10:1;
wherein said hydrogen transfer catalyst is an iridium pincer complex catalyst;
wherein said metathesis catalyst is selected from the group consisting of Schrock catalysts, molybdenum catalysts, tungsten oxide catalysts, rhenium oxide catalysts, and mixtures thereof;
wherein said reacting with a hydrogen transfer catalyst is carried out at a temperature of 120 to 250° C.;
and wherein said reacting with a metathesis catalyst is carried out at a temperature of 30 to 100° C.

2. The method of claim 1, wherein both said hydrogen transfer catalyst and said metathesis catalyst are heterogeneous catalysts.

3. The method of claim 1, wherein said at least one higher molecular weight alkane is produced at a ratio of linear alkanes to branched alkanes of at least 500:1.

4. The method of claim 1, wherein said hydrogen transfer catalyst is immobilized on a solid support, wherein said reaction is carried out in a solvent, and wherein said method further comprises the step of separating free hydrogen transfer catalyst from said solvent.

5. The method of claim 1, wherein said at least one first alkane is linear.

6. The method of claim 1, wherein said at least one first alkane is produced by: converting synthesis gas to said at least one first alkane by Fischer-Tropsch catalysis.

7. The method of claim 1, further comprising the step of:
providing at least a portion of said high molecular weight alkane to a liquid hydrocarbon fuel synthesis process to produce liquid hydrocarbon fuel.

8. The method of claim 1, further comprising the step of:
providing at least a portion of said high molecular weight alkane to a gasoline synthesis process to produce gasoline.

9. The method of claim 1, further comprising the step of:
providing at least a portion of said high molecular weight alkane to a diesel fuel synthesis process to produce diesel fuel.

10. In a method of making a liquid hydrocarbon fuel from a synthesis gas by the Fischer Tropsch reaction, wherein said fuel comprises at least one high molecular weigh alkane, and wherein at least a portion of the product of said Fischer Tropsch reaction comprises at least one low molecular weight alkane, the improvement comprising:
converting at least a portion of said low molecular weight alkane to said high molecular weight alkane by reacting said low molecular weight alkane in the presence of a dual catalyst system comprising: (i) a hydrogen transfer catalyst and (ii) a metathesis catalyst to produce said high molecular weight alkane, said reacting carried out in the presence of a hydrogen acceptor, and wherein the molar ratio of said hydrogen acceptor to said hydrogen transfer catalyst is not greater than 10:1;
wherein said hydrogen transfer catalyst is an iridium pincer complex catalyst;
wherein said metathesis catalyst is selected from the group consisting of Schrock catalysts, molybdenum catalysts, tungsten oxide catalysts, rhenium oxide catalysts, and mixtures thereof;
wherein said reacting with a hydrogen transfer catalyst is carried out at a temperature of 120 to 250° C.;
and wherein said reacting with a metathesis catalyst is carried out at a temperature of 30 to 100° C.

11. The method of claim 10, wherein said both said hydrogen transfer catalyst and said metathesis catalyst are heterogeneous catalysts.

12. The method of claim 10, wherein said at least one higher molecular weight alkane is produced at a ratio of linear alkanes to branched alkanes of at least 500:1, 13. The method of claim 10, wherein said hydrogen transfer catalyst is immobilized on a solid support, wherein said reaction is carried out in a solvent, and wherein said method further comprises the step of separating free hydrogen transfer catalyst from said solvent.

14. The method of claim 10, wherein said fuel is diesel fuel or gasoline.

15. The method of claim 10, wherein:
said at least one low molecular weight alkane is a compound of the formula $C_nH_{2n+2}$ where n is 3-10, and
said at least one high molecular weight alkane is a compound of the formula $C_mH_{2m+2}$,
where m is an integer of from 4 to 40.

16. In a method of making a liquid hydrocarbon fuel from a synthesis gas by the Fischer-Tropsch reaction, wherein said fuel comprises at least one high molecular weigh alkane, wherein at least a portion of the product of said Fischer Tropsch reaction comprises a wax, and wherein said wax is of still higher molecular weight than said high molecular weight alkane, the improvement comprising:
converting at least a portion of said wax to said at least one high molecular weight alkane by reacting said wax in the presence of a dual catalyst system comprising: (i) a hydrogen transfer catalyst and (ii) a metathesis catalyst to produce said at least one higher molecular weight alkane;
wherein said reacting is carried out in the presence of a hydrogen acceptor, and wherein the molar ratio of said hydrogen acceptor to said hydrogen transfer catalyst is not greater than 10:1;
wherein said hydrogen transfer catalyst is an iridium pincer complex catalyst;
wherein said metathesis catalyst is selected from the group consisting of Schrock catalysts, molybdenum catalysts, tungsten oxide catalysts, rhenium oxide catalysts, and mixtures thereof;
wherein said reacting with a hydrogen transfer catalyst is carried out at a temperature of 120 to 250° C.;
and wherein said reacting with a metathesis catalyst is carried out at a temperature of 30 to 100° C.

17. The method of claim 16, wherein said both said hydrogen transfer catalyst and said metathesis catalyst are heterogeneous catalysts.

18. The method of claim 16, wherein said at least one higher molecular weight alkane is produced at a ratio of linear alkanes to branched alkanes of at least 500:1.

19. The method of claim 16, wherein said fuel is diesel fuel or gasoline.

20. The method of claim 16, wherein:
said at least one higher molecular weight alkane is a compound of the formula $C_mH_{2m+2}$, where m is an integer of from 4 to 40;
said wax comprises a compound of the formula $C_pH_{2p+2}$ where p is 18 to 200.

21. The method of claim 1, wherein said reacting step is carried out at atmospheric pressure at a temperature not greater than 200° C.

22. The method of claim 1, wherein said hydrogen transfer catalyst is a homogeneous catalyst;
wherein said alkane is provided as a mixed composition comprising both alkanes and alkenes, with the weight ratio of alkanes to alkenes being at least 50:1;
and wherein the at least one higher molecular weigh alkane produced by the reaction comprises a mixture of linear alkanes to branched alkanes at a molar ratio of at least 1000:1.

23. The method of claim 10, wherein said reacting step is carried out at atmospheric pressure at a temperature not greater than 200° C.

24. The method of claim 10, wherein said hydrogen transfer catalyst is a homogeneous catalyst;
wherein said alkane is provided as a mixed composition comprising both alkanes and alkenes, with the weight ratio of alkanes to alkenes being at least 50:1;
and wherein the at least one higher molecular weigh alkane produced by the reaction comprises a mixture of linear alkanes to branched alkanes at a molar ratio of at least 1000:1.

25. The method of claim 16, wherein said reacting step is carried out at atmospheric pressure at a temperature not greater than 200° C.

26. The method of claim 16, wherein said hydrogen transfer catalyst is a homogeneous catalyst;
wherein said alkane is provided as a mixed composition comprising both alkanes and alkenes, with the weight ratio of alkanes to alkenes being at least 50:1;
and wherein the at least one higher molecular weigh alkane produced by the reaction comprises a mixture of linear alkanes to branched alkanes at a molar ratio of at least 1000:1.

* * * * *